| United States Patent [19] | [11] Patent Number: 4,925,989 |
|---|---|
| Hagan et al. | [45] Date of Patent: May 15, 1990 |

[54] MTBE PREPARATION FROM ISOBUTYLENE/TBA AND METHANOL IN PRESENCE OF AN ACID RESIN CATALYST

[75] Inventors: John J. Hagan, Spring, Tex.; Sheldon Herbstman, Spring Valley, N.Y.

[73] Assignee: Texaco Inc., White Plains, N.Y.

[21] Appl. No.: 56,509

[22] Filed: Jun. 1, 1987

[51] Int. Cl.$^5$ .............................................. C07C 41/06
[52] U.S. Cl. ..................................... 568/697; 568/698
[58] Field of Search ................................. 568/697, 698

[56] References Cited

U.S. PATENT DOCUMENTS

| 2,746,938 | 5/1956 | Ehm et al. | 568/698 |
|---|---|---|---|
| 3,267,157 | 8/1966 | Hansen | 568/698 |
| 4,282,389 | 8/1981 | Droste et al. | 568/697 |
| 4,336,407 | 6/1982 | Smith | 568/697 |

*Primary Examiner*—Howard T. Mars
*Attorney, Agent, or Firm*—Robert A. Kulason; James J. O'Loughlin; Vincent A. Mallare

[57] ABSTRACT

A process for preparing methyl tertiary-butyl ether wherein tertiary-butyl alcohol, isobutylene and methanol are continuously fed into a combination reactor distillation tower having a packed sulfonic acid resin catalyst beds where a substantially pure product of MTBE methyl tertiary-butyl ether is produced.

1 Claim, 1 Drawing Sheet

MTBE PREPARATION FROM ISOBUTYLENE/TBA AND METHANOL IN PRESENCE OF AN ACID RESIN CATALYST

FIELD OF THE INVENTION

The present invention relates to a process for the preparation of tertiary-alkyl ethers and, more particularly, to the preparation of ethers such as methyl-t-butyl ether (MTBE) and t-amyl methyl ether (TAME).

BACKGROUND OF THE INVENTION

Recent concern with environmental pollution by lead from the exhaust gases of internal combustion engines has forced a transition away from the use of lead antiknock compounds in gasoline. In order to produce unleaded gasoline having an acceptable octane value without varying the compounding ratio of gasoline, it has become necessary to use organic blending compounds with high octane ratings.

A variety of organic compounds are known as fuel extenders and octane value improving agents. Particularly, the well known organic compounds include methyl t-butyl ether (MTBE), ethyl t-butyl ether, isopropyl t-butyl ether, t-amyl methyl ether (TAME) and t-butyl alcohol (TBA). The preparation of these ethers and alcohols by the catalytic addition of an alcohol or water to an olefin having a double bond on a tertiary carbon atom has been extensively studied.

In the past and presently, there have been, and are, many processes developed, and being developed, to produce methyl t-butyl ether (MTBE). For the most part, these processes have involved several steps and have been comprehensive as well as being costly. The problem being that only a substantially pure product of MTBE is useful in fuels. Contaminated fuels are not effective and require further treatment to be useful in fuels.

Thus, it is an object of the present invention to provide a one-step process for producing a product of a substantially pure t-alkyl ether such as MTBE or TAME.

DISCLOSURE STATEMENT

U.S. Pat. No. 2,480,940 discloses catalysts employed for the etherification or alcoholification of olefins which have been acids such as $H_2SO_4$, Lewis acids, platinum metal salts and various heterogenous catalysts, and discloses solid sulfonated organic resins that may be used for ion exchange applications.

U.S. Pat. No. 4,071,567 discloses a two-step process for preparing methyl t-butyl ether with methanol and isobutylene in the presence of an acid ion exchange resin.

U.S. Pat. No. 4,198,530 discloses a two-step process for preparing tertiary butyl methyl ether from isobutene and methanol in the presence of an acidic ion exchange catalyst.

SUMMARY OF THE INVENTION

The present invention provides a method of preparing methyl t-butyl ether (MTBE). The process comprises continuously feeding t-butyl alcohol (TBA), isobutylene and methanol (MeOH) into a packed solid-acid catalyst bed, in a reactor-separator distillation column in the presence of the solid-acid catalyst, whereby a product of substantially pure (MTBE) is separated from the reaction mixture.

The process is carried out at a temperature of about 150° F. to about 250° F. and under a pressure of between about 0.50 and about 200 psi.

The basis of the present invention is the fact that both the tertiary-butyl alcohol-methanol and isobutylene-methanol reactions to yield methyl tertiary-butyl ether are equilibrium controlled. Therefore, in the tertiary-butyl alcohol-methanol reaction, for example, if the methyl tertiary-butyl ether is continuously removed from the reaction zone by distillation, the reaction theoretically can go to completion. For example,

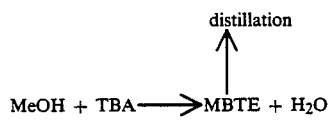

The process is also arranged so that the product water continuously drops out of the reaction zone since it is heavier than the other components of the equilibrium mixture and, thus too, drives the equilibrium controlled reaction towards completion. Therefore, the combination of (a) a reactions zone containing active catalysts and (b) distillation capability in a single unit uniquely adapts itself to the tertiary-butyl alcohol-methanol and isobutylene-methanol reactions to yield high purity methyl tertiary-butyl ether.

DETAILED DESCRIPTION OF THE INVENTION

Figure 1:
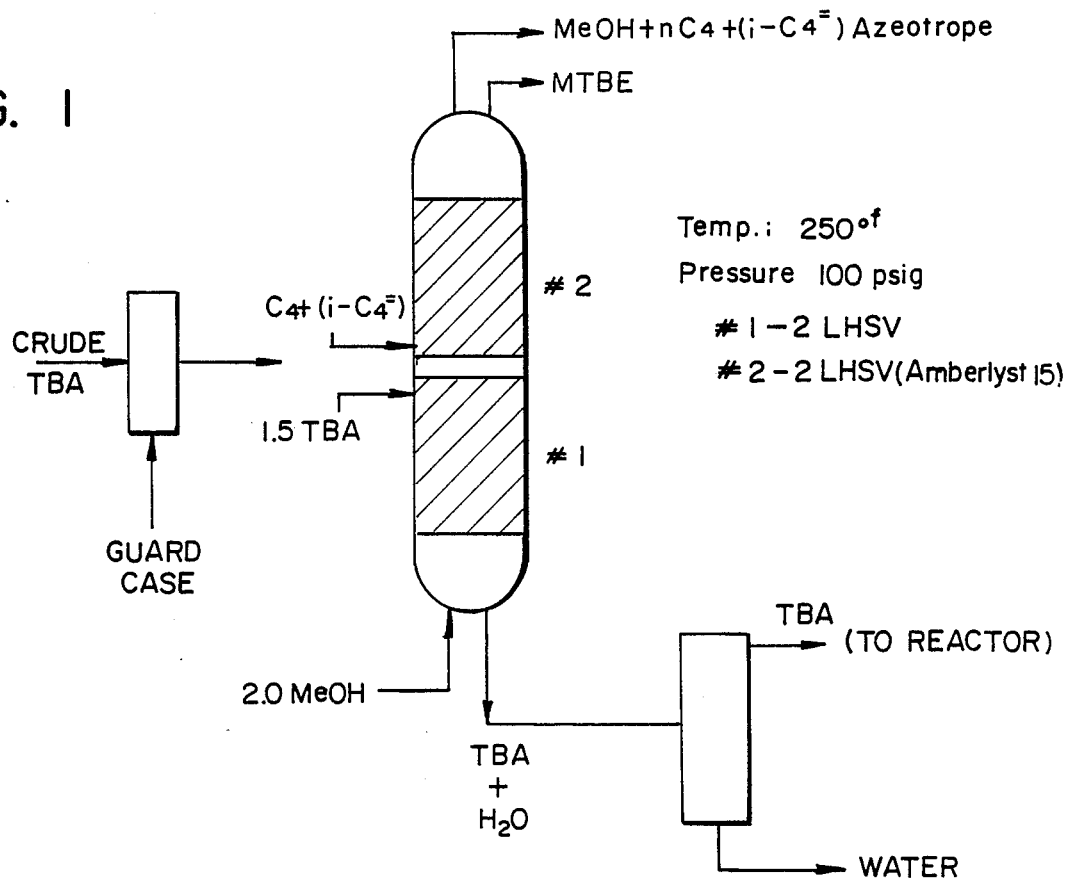

Although the invention will be described with specific reference to the preparation of methyl t-butyl ether (MTBE) for the purpose of clarity, it should be understood that other ethers and alcohols prepared by the catalytic addition of alcohol or water to olefins having a double bond at the tertiary carbon are within the scope of the present invention. Such olefins include isobutylene, 2-methyl butene-1, 2methyl butene-2, 2-methyl penten-1 and 2-methyl pentene-2.

The process that may be used for preparing MTBE according to the present invention is illustrated by the following equation:

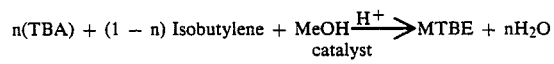

(where n is less than 1.0)

The basis for the present invention is that the combined streams of isobutylene and TBA can be reacted with MeOH over a sulfonic acid resin catalyst, in one-step, to yield MTBE.

Tertiary alkyl ethers, such as methyl t-butyl ether (MTBE) and t-amyl methyl ether (TAME) are useful as fuel extenders and, in particular, as gasoline octane enhancers. Generally, processes for producing these materials all rely on a primary alcohol and an olefin which contains a double-bond on a tertiary carbon as raw materials. The reactions are carried out in the liquid phase in which ion exchange resins in their acid form are particularly suitable for the present reaction.

The optimum results are obtained when macroreticular resins are used such as the Amberlyst 15 catalysts. The catalyst, i.e., a solid-acid catalyst may be Amberlyst 15 or Nafion-H resin catalysts. The preferred catalysts are the Amberlyst 15 catalysts.

The catalyst is packed in a distillation tower and is substantially insoluble to the liquid components therein. The catalyst can be present in the column either undiluted or with an inert diluent in weight ratios of as little as 200/1 of inert to catalyst.

The process of the present invention and a condensation phase of the components (i.e., methyl tertiary-butyl ether, methanol, tertiary-butyl alcohol, isobutylene and $H_2O$) are illustrated in the attached drawings which is FIG. 1 is a flow diagram of the present reaction process showing the equipment used therefor and the material flow thereof.

In the present process, isobutylene and tertiary-butyl alcohol is used to produce methyl tertiary-butyl ether. Tertiary-butyl alcohol is conventionally produced in large quantities from processes for producing propylene oxide from propylene. The subject of the present invention is a one-step process which makes it possible to achieve high conversions of isobutylene/tertiary-butyl alcohol and methanol to methyl tertiary-butyl ether using a distillation column as the reactor and primary separator.

An object of the present invention is to obtain a product stream which is substantially methyl tertiary-butyl ether and substantially free of water, isobutylene, tertiary-butyl alcohol and methanol. This can be accomplished by catalytic distillation in a combination reactor and distillation column that has been packed with acidic resin catalysts. Under these conditions, as it is formed in the reaction, low-boiling methyl tertiary-butyl ether is removed at the top of the reactor distillation column and by-product water is removed at the bottom of the column. Adding isobutylene and tertiary-butyl alcohol at the middle catalyst bed of the catalyst bed, and methanol near the bottom of the column, results in a dual mass action effect.

The tert-butyl alcohol (tertiary-butyl alcohol) being relatively more dense material, continuously drops down the column while isobutylene, being a gas under reaction conditions, continuously rises up the column. Near the bottom of the column, where methanol is in excess, the conversion of tertiary-butyl alcohol to methyl tertiary-butyl ether is nearly complete and unreacted tertiary-butyl alcohol is present in the bottoms. Near the top of the column where isobutylene and tertiary-butyl alcohol is in excess, the conversion of unreacted methanol to methyl tertiary-butyl ether is complete and very little methanol is present in the overhead. The advantage of minimizing the presence of unreacted methanol is that it minimizes the need for auxiliary separation towers to purify methyl tertiary-butyl ether by separating it from unreacted methanol. Above the point at which isobutylene and tertiary-butyl alcohol enters the column at the top of the catalyst beds, the distillation trays contain only unreacted isobutylene, methyl tertiary-butyl ether and small amounts of methanol which can be easily separated in ascending trays. Below the point at which methanol is added, the distillation trays contain only water and tert-butanol which can be easily separated in descending trays.

The distillation tower or column may have one or two packed catalyst beds depending on the choice and preference of design.

The reaction can be carried out at a temperature of about 150° to about 250° F., preferably from about 165° to about 170° F. and under a pressure of about 50 psi to about 200 psi, preferably about 100 psi. The liquid flow rate of the materials in the reaction ranges from about 1.0 to about 10.0 LHSV. The preferred liquid flow rate is about 2.0 LHSV.

The charge of the present process is fed in a molar ratio of methanol/(tertiary-butyl alcohol+isobutylene) of between about 1:1 and about 10:1; and the molar ratio of MeOH/TBA/isobutylene is about 2.0/1.5/0.5.

In contrast to known processes where either tertiary-butyl alcohol or isobutylene is used with methanol to prepare methyl tertiary-butyl ether, the present process uses both tertiary-butyl alcohol and isobutylene to prepare methyl tertiary-butyl ether. The advantages for using the combination of $C_4$ components are:

1. The combination gives the operation of the process increased flexibility since there are times when both components (isobutylene and tertiary-butyl alcohol) are available and could be used in combination. The run conditions described (Example I) below are equally suitable for either tertiary-butyl alcohol+methanol or isobutylene+methanol or combinations of tertiary-butyl alcohol+isobutylene.

2. The reaction of isobutylene+methanol is very exothermic while the reaction of tertiary-butyl alcohol+methanol is slightly endothermic. The exothermic reaction will supply heat to the distillation of the methyl tertiary-butyl ether product and, therefore, the combination (isobutylene+tertiary-butyl alcohol) would be the most efficient use of heat energy. Otherwise, this energy would be wasted.

3. The presence of isobutylene in the reaction zone drives the reaction to completion snce (a) it reacts with water which is formed and prevents the reverse reaction, i.e., splitting of methyl tertiary-butyl ether as shown in the equations:

$$TBA + MeOH \rightarrow MTBE + H_2O$$

$$Isobutylene + H_2O \rightarrow TBA \text{ (to reaction)}$$

(b) with unreacted methanol to drive the reaction to completion. Therefore, the substantially pure methyl tertiary-butyl ether results as illustrated by the following equation:

$$Unreacted\ MeOH + Isobutylene \rightarrow MTBE$$

Thus, as indicated above, the introduction of isobutylene at the mid-point or top of the reactor will drive the reactions to completion.

Referring to FIG. 1, a typical reaction process according to the present invention is illustrated with the flow of the feed (charge) components the products and unreacted charge components. The flow rates of the feed components, products, etc. are provided below in Table I.

The advantages of present invention will be more apparent when considering the following example which described the present process illustrated in FIG. 1 for producing methyl tertiary-butyl ether.

EXAMPLE I

In this example, crude tert-butyl alcohol is initially purified of acids and hydroperoxides by running it through a guard case containing an absorbent consisting of sodium oxide-cobalt oxide on activated alumina. Then, the purified TBA is used in the process as illustrated in FIG. 1.

A combination reactor-distillation column is used in the process. The bottom portion of the reactor contains a single or double beds of resin catalyst and distillation trays, while the top part of the reactor contains distillation trays and a take-off line for separation of products. Below the catalyst beds are lines for the introduction of methanol and the take-off of unreacted tert-butyl alcohol and water which is a reaction product.

The preferred reaction conditions of the process are a temperature of about 165°–170° F. and a pressure of about 100 psig. Methanol is continuously pumped at the rate of 32 lb/hr (2 mole lb/hr) in the upflow made up catalyst bed No. 1 packed with an Amberlyst 15 resin catalyst. Meanwhile, tertiary-butyl alcohol is continuously pumped at the rate of 108 lb/hr (1.5 mole lb/hr) into the top of catalyst bed No. 1. As the tertiary-butyl alcohol descends the column it contacts and reacts with the methanol to yield methyl tertiary-butyl ether and water. The dense water phase continuously drops down the reactor along with some unreacted tertiary-butyl alcohol, while the lighter methyl tertiary-butyl ether product plus unreacted methanol rise up the column where at the entrance to catalyst bed No. 2 tertiary-butyl alcohol contacts isobutylene which is being continuously introduced at the rate of 28 lb/hr (0.5 mole lb/hr). The isobutylene reacts with unreacted methanol in the methyl tertiary-butyl ether-methanol product stream. The reaction product which is almost pure methyl tertiary-butyl ether is continuously distilled out of the reaction zone at the top of catalyst bed No. 2 (packed with Amberlyst 15 catalyst) along with small amounts of unreacted isobutylene and methanol.

The compositions of the proposed charge materials, estimated product of the example above and process shown in FIG. 1, are provided below in Table I.

TABLE I

| PROCESS FOR MTBE OVERALL STOICHIOMETRY | |
| --- | --- |
| Charge Materials | Products/Unreacted Materials |
| MeOH (64 lb/hr, 2.0 mole lb/hr) | MTBE (146 lb/hr, 1.7 mole lb/hr) |
| TBA (108 lb/hr, 1.5 mole lb/hr) | MeOH (9.6 lb/hr, 0.3 mole lb/hr) |
| Isobutylene (28 lb/hr, 0.5 mole lb/hr | Isobutylene (11.2 lb/hr, 0.2 mole lb/hr, H$_2$O (25 lb/hr, 1.4 mole-lb/hr |

The estimate average yield of methyl tertiary-butyl ester is calculated as follows:

$$\text{Percent yield} = \frac{1.7 \text{ mole (MTBE/Hr)}}{2.0 \text{ mole (Isobutylene + TBA/hr)}}$$

Percent yield = 85.0 percent

In review of the present process, it can be assumed that the yield of methyl tertiary-butyl ether is at least about 85.0 percent.

The present invention as described above may be modified in many ways by those of ordinary skill in the art without departing from the scope of the invention as set forth in the appending claims.

We claim:

1. A method of producing MTBE comprising feeding a mixture of TBA and isobutylene with methanol into a distillation column having a packed sulfonic acid resin catalyst bed wherein said isobutylene is fed near the top of the bed, TBA at the middle of the bed and methanol in the bottom of the bed to react said components and separate therefrom a substantially pure MTBE product.

* * * * *